United States Patent
Oosterbaan et al.

(10) Patent No.: US 6,696,496 B2
(45) Date of Patent: Feb. 24, 2004

(54) LOW WATER-SOLUBLE VENLAFAXINE SALTS

(75) Inventors: Marinus J. M. Oosterbaan, Nijmegen (NL); Rolf Keltjens, Nijmegen (NL)

(73) Assignee: Synthon BV, Nijmegen (NL)

( * ) Notice: Subject to any disclaimer, the term of this patent is extended or adjusted under 35 U.S.C. 154(b) by 0 days.

(21) Appl. No.: 10/397,380

(22) Filed: Mar. 27, 2003

(65) Prior Publication Data

US 2003/0190353 A1 Oct. 9, 2003

Related U.S. Application Data

(60) Provisional application No. 60/367,704, filed on Mar. 28, 2002, and provisional application No. 60/372,447, filed on Apr. 16, 2002.

(51) Int. Cl.[7] .................... A01N 33/02; A61K 31/135; A61K 9/20; A61K 9/14; C07C 57/18
(52) U.S. Cl. ................. 514/648; 562/595; 424/451; 424/452; 424/464; 424/465; 424/468; 424/489
(58) Field of Search ............... 562/595; 514/648; 424/451, 452, 464, 465, 468, 489

(56) References Cited

U.S. PATENT DOCUMENTS

| | | | |
|---|---|---|---|
| 4,535,186 A | | 8/1985 | Husbands et al. |
| 5,043,466 A | | 8/1991 | Shepard |
| 5,744,474 A | * | 4/1998 | Thor |
| 5,916,923 A | | 6/1999 | Rudolph et al. |
| 6,096,339 A | * | 8/2000 | Ayer et al. |
| 6,197,828 B1 | | 3/2001 | Jerussi et al. |
| 6,274,171 B1 | | 8/2001 | Sherman et al. |
| 6,403,120 B1 | | 6/2002 | Sherman et al. |
| 6,419,958 B2 | | 7/2002 | Sherman et al. |
| 6,444,708 B2 | | 9/2002 | Rudolph et al. |
| 6,599,529 B1 | * | 7/2003 | Skinhoj et al. |
| 2001/0012855 A1 | | 8/2001 | Rudolph et al. |
| 2001/0055612 A1 | | 12/2001 | Sherman et al. |
| 2002/0006443 A1 | | 1/2002 | Curatolo et al. |

FOREIGN PATENT DOCUMENTS

| | | |
|---|---|---|
| CN | 1225356 | 8/1999 |
| CN | 1240206 | 1/2000 |
| EP | 0797991 A1 | 10/1997 |
| WO | WO99/22724 A2 | 5/1999 |
| WO | WO00/32556 A1 | 6/2000 |
| WO | WO00/76955 A1 | 12/2000 |
| WO | WO01/07397 A1 | 2/2001 |
| WO | WO02/45658 A2 | 6/2002 |

OTHER PUBLICATIONS

Zhang et al., "Novel Isomerization Reaction of N,N–Dimethyl–α–(methoxycarbonyl)–4 – substituted – benzylammonium N–Methylides," J. Org. Chem. vol. 64, 1999, pp. 581–586.

Roberts et al., "Addition of Eschenmoser's salt to Ketone, Ester, & Lactone Enolates. A Convenient Synthesis of α–Methylene Carbonyls Via Mannich Intermediates," Tetrahedron Letters No. 19, 1977, pp. 1621–1624.

S. Jane deSolms, "N,N,N',N'–Tetramethylmethanediamine. A Simple, Effective Mannich Reagent," J. Org. Chem. vol. 41, No. 15, 1976, pp. 2650–2651.

Yardley, et al., "2–Phenyl–2–(1–dydroxycycloalkyl) ethylamine Derivatives: Synthesis and Antidepressant Activity," J. Med. Chem., vol. 33, 1990, pp. 2899–2905.

Makhija et al., "Once Daily Sustained Release Tablets of Venlafaxine, A Novel Antidepressant," European Journal of Pharmaceutics and Biopharmaceutics, vol. 51, 2002, pp. 9–15.

Nenitzescu et al., "The Syntheis of Cyclic Alcohols and Olefins by the Interaction of Dimagnesium Halides and Esters," The Laboratory of Organic Chemistry, Scoala Politehnica, 1950, pp. 3483–3486.

* cited by examiner

Primary Examiner—Thurman K. Page
Assistant Examiner—Humera N. Sheikh
(74) Attorney, Agent, or Firm—Mark R. Buscher

(57) ABSTRACT

Low water soluble salts of venlafaxine, especially venlafaxine maleate, are provided. Such salts can provide a variety of dosage forms including hydrogel-based extended release dosage forms.

25 Claims, No Drawings

LOW WATER-SOLUBLE VENLAFAXINE SALTS

This application claims the benefit of priority under 35 U.S.C. §119 from U.S. provisional application serial No. 60/367,704, filed Mar. 28, 2002 and from U.S. provisional application serial No. 60/372,447, filed Apr. 16, 2002; the entire contents of each application being incorporated herein by reference.

BACKGROUND OF THE INVENTION

The present invention relates to low water-soluble venlafaxine salts, especially venlafaxine maleate, various forms thereof, and the use of the same in pharmaceutical compositions for treating depression and other conditions.

Venlafaxine is the common name for the compound 1-[2-(dimethylamino)-1-(4-methoxyphenyl) ethyl] cyclohexanol, having the structure shown below.

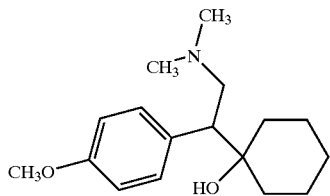

U.S. Pat. No. 4,535,186 describes a class of hydroxycycloalkanephenethyl amines as being useful antidepressants and exemplifies the compound now known as venlafaxine hydrochloride as one of the suitable species. Venlafaxine hydrochloride is approved for sale in various countries including the United States of America. It is available as an immediate release tablet and as an extended release capsule, under the brand name EFFEXOR® (Wyeth Ayerst) and EFFEXOR XR® (Wyeth Ayerst) respectively.

Venlafaxine has been the subject of various research endeavors. For example, U.S. Pat. No. 5,043,466 describes a process for making cyclohexanol derivatives in a specified solvent composition. Example 3 of this patent shows the synthesis of venlafaxine as the hydrochloride salt thereof.

U.S. Pat. No. 6,274,171 and related EP 0 797 991A1 disclose encapsulated extended release formulations for venlafaxine hydrochloride. These patents indicate that commercial venlafaxine hydrochloride tablets were administered two or three times daily, but that due to variations in the drug concentration in the patient's blood plasma caused by such a dosing regimen, unwanted side effects, especially nausea and vomiting were common. A once daily, encapsulated extended release dosage form is disclosed that provides a flattened drug plasma profile and reduces these side effects. The encapsulated dosage form is taught to comprise spheroids of venlafaxine hydrochloride, microcrystalline cellulose, and hydroxypropylmethylcellulose (HPMC). These spheroids are coated with a mixture of ethyl cellulose and HPMC. By providing an appropriate amount of the coating, the desired blood plasma profile can be obtained. An acceptable batch of coated spheroids will meet the following in vitro dissolution profile:

| Time (hours) | Average % venlafaxine hydrochloride released |
|---|---|
| 2 | <30 |
| 4 | 30–55 |
| 8 | 55–80 |
| 12 | 65–90 |
| 24 | >80 | using USP Apparatus 1 (basket) at 100 rpm in purified water at 37° C. The coated spheroids can be from a single batch or represent a blend of different batches.

U.S. Pat. No. 6,274,171 and EP 0 797 991 also state that forming an extended release dosage form of venlafaxine hydrochloride was difficult in part due to the high water solubility of the hydrochloride salt. In fact, these patents disclose that "[n]umerous attempts to produce extended release tablets by hydrogel technology proved to be fruitless because the compressed tablets were either physically unstable (poor compressibility or capping problems) or dissolved too rapidly in dissolution studies." See U.S. Pat. No. 6,274,171 at column 4, lines 60–65 and EP 0 797 991 at page 3 lines 35–37. Unlike the encapsulated extended release formulations described in these patents, a hydrogel extended release venlafaxine hydrochloride tablet is taught to typically exhibit a dissolution profile wherein 40%–50% is released at 2 hours, 60%–70% is released at 4 hours, and 85%–100% is released at 8 hours.

WO99/22724 also discloses encapsulated venlafaxine hydrochloride extended release dosage forms. These formulations differ from those in U.S. Pat. No. 6,274,171 and EP 0 797 991 in that the spheroid is substantially free of HPMC. Apparently HPMC can be omitted from the spheroid when smaller amounts of venlafaxine hydrochloride are employed.

U.S. Pat. No. 6,197,828 and WO00/32556 discloses the use of individual (+) and (−) enantiomers, respectively, of venlafaxine as well as metabolites thereof. While the commercial venlafaxine hydrochloride is a racemate, these patents teach that various side effects may be reduced by using one isomer substantially without the presence of the other.

Although venlafaxine hydrochloride provides good pharmaceutical activity, it would be beneficial to find other forms of venlafaxine. In particular, venlafaxine forms that are easier handle would be advantageous. Venlafaxine hydrochloride is relatively aggressive towards handling equipment and is irritating to the skin, etc. of human personnel that handle the pure active. A venlafaxine form that is less aggressive and less irritating would be desirable. It is further desirable to provide a venlafaxine form that can be easily formulated into various dosage forms including hydrogel extended release tablets.

SUMMARY OF THE INVENTION

The present invention is based on the discovery of low water-soluble venlafaxine salts. Unlike venlafaxine hydrochloride, the low water-soluble salts of the present invention are more easily formulated into extended release formulations including hydrogel tablets. Thus, a first aspect of the present invention relates to a low water-soluble venlafaxine salt. Such salts exhibit lower water-solubility relative to venlafaxine hydrochloride and preferably 380 mg/ml or less.

A preferred low water-soluble venlafaxine salt is venlafaxine maleate. Accordingly, a second aspect of the invention relates to a venlafaxine maleate compound. The compound can be isolated and/or purified or it can be part of a composition. The compound can be in solid form including crystalline forms but is not limited thereto. A preferred compound is crystalline venlafaxine hydrogenmaleate anhydrate.

Another aspect of the present invention relates to a pharmaceutical composition comprising an effective amount of venlafaxine maleate and a pharmaceutically acceptable excipient. The composition can be an immediate release dosage form or an extended release dosage form and embraces tablets as well as pellets/beads/spheroids or other encapsulated forms. In one embodiment, the venlafaxine maleate is provided in a hydrogel tablet. The hydrogel tablet preferably provides sufficient extended release so that the tablet is a once daily dosage form.

An additional aspect of the present invention relates to a pharmaceutical composition comprising a low water-soluble venlafaxine salt and a hydrophilic matrix material. Such a composition includes finished hydrogel tablets as well as tabletting powder blends and other intermediates in making a final dosage form. The hydrogel tablet exhibits extended release such that no more than twice daily dosing and preferably once daily dosing can be achieved.

A further aspect of the invention relates to the use of a low water-soluble venlafaxine salt, and in particular venlafaxine maleate, in treating venlafaxine-treatable diseases or conditions. Hence the invention provides a method for treating a venlafaxine-treatable disease or condition, which comprises administering to a patient in need thereof an effective amount of a low water-soluble venlafaxine salt such as venlafaxine maleate. The low water-soluble salt is typically administered as an oral composition such as a tablet or capsule and is preferably administered once daily.

DETAILED DESCRIPTION OF THE INVENTION

The present invention is based on the surprising discovery that various salts of venlafaxine are low water-soluble relative to the water solubility of venlafaxine hydrochloride. As used herein "low water-soluble" venlafaxine salt means that the salt exhibits a water solubility that is less than two thirds the water solubility of venlafaxine hydrochloride, preferably less than half, more preferably one third and more preferably less than one quarter the water solubility of venlafaxine hydrochloride. In absolute values, a low water-soluble salt of venlafaxine preferably has a water solubility of 380 mg/ml or less, preferably 200 mg/ml or less, more preferably 150 mg/ml or less.

Such low water soluble salts include venlafaxine maleate compounds and venlafaxine benzenesulfonate (besylate) compounds and is expected to also include venlafaxine fumarate compounds, but is not limited thereto. Any salt of venlafaxine that exhibits a solubility within the above range is included within the meaning of low water soluble salts. Venlafaxine besylate compounds are more fully described in U.S. provisional patent application serial No. 60/367,734, filed Mar. 28, 2002, entitled "Venlafaxine Besylate," the entire contents of which are incorporated herein by reference. For simplicity, the present invention will be described with reference to a venlafaxine maleate compound, but it should be understood that it equally applies to all low water-soluble venlafaxine salts.

A venlafaxine maleate compound is any form of the salt formed by venlafaxine and maleic acid. Typically the venlafaxine and maleate moieties are present in about a 1:1 molar ratio, which is referred to herein as "venlafaxine hydrogenmaleate." However, other ratios such as 2:1 or 3:2 are also possible due to the fact that maleic acid contains two acid groups, each having the potential to from a salt with a venlafaxine moiety. In addition, venlafaxine maleate is less aggressive, less irritating, and easier to handle than venlafaxine hydrochloride. Note that maleic acid is generally easier to handle than hydrochloric acid. Accordingly, venlafaxine maleate is easier to formulate into a variety of dosage forms, especially extended release dosage forms, than venlafaxine hydrochloride. The preferred form is the venlafaxine hydrogenmaleate.

Venlafaxine maleate compounds are low-water soluble venlafaxine salts. For example, venlafaxine hydrogenmaleate anhydrate exhibits a water solubility of about 370 mg/ml, i.e. 368 mg/ml, while venlafaxine hydrochloride exhibits a water solubility of about 570 mg/ml at ambient conditions.

The venlafaxine in the venlafaxine maleate compound of the present invention can be any form of venlafaxine. For example, venlafaxine has one optically active carbon, thus allowing for existence of two enantiomers and a racemate. Both enantiomers are pharmaceutically active. The venlafaxine maleate compound can be based on the racemate or mixture of enantiomers of venlafaxine or on the pure or substantially pure (+) or (−) enantiomer of venlafaxine (hereinafter referred to as (+)-venlafaxine maleate and (−)-venlafaxine maleate): all are included within the meaning of "venlafaxine maleate" unless specifically noted otherwise.

The compound can be in isolated and/or purified form, but such is not required. The compound includes various physical forms of the salt including dissolved forms, oil or liquid forms, and solid forms including amorphous and crystalline forms.

The compound is typically in a crystalline form. Crystalline forms include venlafaxine maleate anhydrates, hydrates, and solvates. Preferably the venlafaxine maleate is venlafaxine maleate anhydrate, more preferably venlafaxine hydrogenmaleate anhydrate.

A venlafaxine maleate compound can be prepared by contacting a venlafaxine substrate with a maleate substrate. Typically the contacting occurs in a suitable solvent system. The venlafaxine maleate product can be isolated, if desired, by precipitation, evaporation, spray drying, or other conventional techniques known in the art.

The "venlafaxine substrate" includes any substance that provides a venlafaxine moiety or ion thereof and specifically includes racemic and enantiomeric venlafaxine base, a venlafaxine salt other than venlafaxine maleate, e.g. venlafaxine HCl, or a raw venlafaxine, i.e. a reaction product or reaction mixture comprising venlafaxine that has been obtained after the last step of production of venlafaxine. The venlafaxine substrate can be obtained by conventional processes and synthesis schemes known in the art. For example, U.S. Pat. Nos. 4,535,186, 5,043,466, and 6,197,828 all teach methods for making venlafaxine. Venlafaxine base in its isolated state is obtainable by neutralization of venlafaxine hydrochloride, extraction by ethyl acetate and evaporation of the solvent, according to the method disclosed in U.S. Pat. No. 6,197, 828 and WO 00-32566. Alternatively, venlafaxine base can be obtained as a precipitate, preferably a filtratable precipitate, by the use of a contrasolvent, e.g. heptane, optionally with cooling and/or solvent removal, without the need to convert to a salt, as is more fully described in U.S. provisional patent application serial No. 60/367,736, filed Mar. 28, 2002, entitled "Venlafaxine Free Base," the entire contents of which are incorporated herein by reference.

Single enantiomers of venlafaxine free base can be made as described in J.Med.Chem. 1990, 33 (10), 2899–2905. Venlafaxine hydrochloride is commercially available and can be produced according to U.S. Pat. No. 4,535,186, EP 112669, U.S. Pat. Nos. 5,043,466, 6,197,828 and WO 01-07397. Other salts can be formed by methods analogous to those disclosed in these cited patent documents.

The "maleate substrate" includes any substance that provides a maleic acid moiety or ion thereof and specifically includes any form of maleic acid as well as a salt of maleic acid with a base. A preferred substrate is maleic acid. Maleate substrates are commercially available and/or may be prepared by methods known in the prior art.

The molar ratio of the substrates is not particularly limited and is generally about stoichiometric to the desired ratio. Typically a slight excess of maleate substrate is used. Commonly the molar ratio of venlafaxine substrate to maleate substrate is within the range of 0.8:1 to 1.2:1, more typically 0.9:1 to 1.1:1 or about 1:1. However, up to a significant excess of one substrate, especially the maleate substrate can be used. Such excess of either maleate or venlafaxine is typically in the range of 1.1 to 3.0:1, more typically 1.1 to 2:1. For economy reasons, excesses are normally kept small and typically the excess maleate substrate, if any, is provided in slight stoichiometric excess such as 1.01 to 1.5 times the molar amount of venlafaxine.

The solvent system is preferably selected so as to facilitate the salt reaction and to allow subsequent separation of the resulting maleate. Advantageously, both venlafaxine substrate and the maleate substrate are dissolvable in the solvent system, at least at elevated temperatures. In the process, a mixture, slurry, or solution of venlafaxine substrate and a solvent may be contacted with a maleate substrate, or conversely, a mixture, slurry, or solution of maleate substrate and a solvent may be contacted with venlafaxine substrate. In another embodiment, both partners may be combined with a solvent system prior to being contacted together, whereby the solvent system used for maleate substrate may be identical with or different from the solvent system used for the venlafaxine substrate. The solvent system can be comprised of a single solvent or a mixture of solvents. When two or more solvents are used, a two phase reaction scheme may be used wherein the venlafaxine substrate and maleate substrate are primarily reacted in one phase and the resulting venlafaxine maleate compound is primarily present in the other phase due to, inter alia, solubility differences, etc. Suitable solvents include water, a lower alcohol ($C_1$–$C_6$) such as methanol or ethanol, an aliphatic ketone such as acetone, an ether such as dioxane, an ester such as ethyl acetate, and mixtures thereof.

The temperature of contact of both substrates in the solvent system is from ambient to the boiling point of the solvent system, the later being preferred. It is not required that a complete solution is formed in this step, i.e. a slurry or two phase solution are also possible, though a single solution is generally preferred.

The venlafaxine maleate compound can be isolated or recovered from the salt forming reaction by any convenient means. For example, the venlafaxine maleate compound can be precipitated out of a solution or reaction mixture. The precipitation may be spontaneous depending upon the solvent system used and the conditions. Alternatively, the precipitation can be induced by reducing the temperature of the solvent, especially if the initial temperature at contact is elevated. The precipitation may also be facilitated by reducing the volume of the solution/solvent or by adding a contra solvent, i.e. a liquid miscible with the solvent in which the venlafaxine maleate is less soluble. Seed crystals of venlafaxine maleate may also be added to help induce precipitation. The precipitated venlafaxine maleate compound can be isolated by conventional methods such as filtration or centrifugation, optionally washed and dried, preferably under diminished pressure.

Alternatively, the venlafaxine maleate compound can be isolated by evaporating away the solvent and collecting the residue. Such a method generally leads to an oil or solid amorphous form of venlafaxine maleate. Similarly, an amorphous solid form of the venlafaxine maleate compound can be recovered by spray drying or freeze drying a solution containing the venlafaxine maleate compound.

In a preferred mode, venlafaxine base is dissolved in acetone under heating, maleic acid is added to the solution under stirring, the mixture is heated to complete dissolution and the clear solution is allowed to cool. Venlafaxine maleate anhydrate crystallizes from the solution and is separated by filtration and dried.

Venlafaxine maleate prepared in solid state may be, if necessary, purified to the desired degree of purity. Venlafaxine maleate can be purified for instance by a (re) crystallization from a suitable solvent that may be identical or different from the solvent system used for its production. Examples of preferred suitable solvents for a purifying crystallization step are acetone, ethanol, water, and combinations thereof.

Single enantiomers of venlafaxine maleate may be prepared essentially as disclosed above, whereby the venlafaxine substrate comprises the single enantiomer of venlafaxine. Preferred substrates are single enantiomers of venlafaxine base or venlafaxine hydrochloride.

The venlafaxine maleate compound of the present invention can be formulated with a pharmaceutically acceptable excipient into a pharmaceutical composition. The pharmaceutical compositions of the present invention include the unit dosage form as well as the intermediate bulk formulations such as pellets, beads, powder blends, etc. Typically the composition is a finished dosage form also referred to as a unit dose. Dosage forms include oral dosage forms, topical dosage forms such as a transdermal patch, parenteral dosage forms such as an injectable solution, and rectal dosage forms such as a suppository, but is not limited thereto. Oral dosage forms are the most preferred due to the ease of administration and include solid oral dosage forms such as capsules, tablets, sachets/granules, and powders, as well as liquid oral dosage forms such as solutions, suspensions, and emulsions.

Pharmaceutically acceptable excipients are well known in the art and include diluents, fillers, binders, lubricants, disintegrants, glidants, colorants, pigments, taste masking agents, sweeteners, plasticizers, and any acceptable auxiliary substances such as absorption enhancers, penetration enhancers, surfactants, co-surfactants, and specialized oils. The proper excipient(s) are selected based in part on the dosage form, the intended mode of administration, the intended release rate, and manufacturing reliability. Examples of common types of excipients include various polymers, waxes, calcium phosphates, and sugars. Polymers include cellulose and cellulose derivatives such as HPMC, hydroxypropyl cellulose, hydroxyethyl cellulose, microcrystalline cellulose, carboxymethylcellulose, sodium carboxymethylcellulose, calcium carboxymethylcellulose, and ethylcellulose; polyvinylpyrrolidones; polyethylenoxides; and polyacrylic acids including their copolymers and crosslinked polymers thereof, i.e. Carbopol® (B. F.

Goodrich), Eudragit® (Rohm), polycarbophil and chitosan polymers. Waxes include white beeswax, microcrystalline wax, carnauba wax, hydrogenated castor oil, glyceryl behenate, glycerylpalmito stearate, saturated polyglycolyzed glycerate. Calcium phosphates include dibasic calcium phosphate, anhydrous dibasic calcium phosphate, and tribasic calcium phosphate. Sugars include simple sugars such as lactose, maltose, mannitol, fructose, sorbitol, sacarose, xylitol, isomaltose, and glucose as well as complex sugars (polysaccharides) such as maltodextrin, amylodextrin, starches, and modified starches.

Any form of the venlafaxine maleate can be used in the pharmaceutical composition. Preferred venlafaxine maleate forms are: crystalline venlafaxine hydrogenmaleate anhydrate, (+)-venlafaxine maleate anhydrate, and (–)-venlafaxine maleate anhydrate. The amount of venlafaxine maleate compound contained in a unit dosage form is an amount effective to treat one or more venlafaxine-treatable diseases or conditions as is hereinafter defined and can be determined by workers skilled in the art without undue experimentation. Generally this amount ranges from 2 mg to 300 mg. For oral dosage forms the amount is generally from 30 mg to 300 mg per unit dose. Contemplated doses include amounts of about 37.5 mg, 75 mg, 100 mg, 112.5 mg, 150 mg, 200 mg, and 300 mg strengths. For clarity, all amounts of venlafaxine maleate are expressed herein in terms of the weight of the free base contained in the venlafaxine maleate compound, as is conventional in the art.

As mentioned above, oral dosage forms are preferred and include tablets, capsules, sachets/granules, and powders. Tablets can be soluble tablets, dispersible tablets, effervescent tablets, chewable tablets, lyophilized tablets, coated tablets including sugar coatings, enteric coatings, and gastro-soluble coatings, and modified release tablets including microencapsulated active substance tablets, matrix tablets, and coated tablets such as polymer coated extended release tablets and osmotic tablets of the mono-compartmental or bi-compartmental type. Capsules include hard gelatin capsules that can be filled with powder, pellets, granules, small tablets or mini-tablets. The capsule and/or the material placed within can be coated such as for enteric release or modified release. Soft capsules are also included and are more typically filled with liquids or dispersions, but are not limited thereto. Sachets or granules can be effervescent granules, coated granules, enteric granules, or modified release granules.

One embodiment of the present invention relates to an immediate release tablet. An "immediate release" as used herein means that at least 80% of the venlafaxine maleate in the tablet is dissolved by 30 minutes under a dissolution test using USP Apparatus 1 (basket) at 100 rpm in purified water at 37° C. Any conventional immediate release composition can be used in formulating the venlafaxine maleate immediate release tablet. Typically such tablets contain one or more binders and/or diluents such as HPMC, microcrystalline cellulose, a calcium phosphate, lactose, and mannitol; a lubricant such as magnesium stearate; and optionally a disintegrant such as sodium starch glycollate, crosscarmellose or crosspovidone. Additional excipients such as colorants, antioxidants, etc can also be present.

More preferably, however, the solid oral dosage form is an extended release dosage form. This can be accomplished in either a tablet or a capsule form. An extended release dosage form as used herein means that in a dissolution test using USP Apparatus 1 (basket) at 100 rpm in purified water at 37° C., less than 80% of the venlafaxine maleate is dissolved during the first two hours, more typically less than 50%, and preferably less than 30% of the venlafaxine maleate is dissolved during the first two hours. Extended release tablets or capsules generally allow for twice a day, or more preferably once a day dosing, to provide 24 hour therapeutic blood plasma levels of venlafaxine to the patient. In this regard, the most preferred dosage form is one which provides once daily dosing. Such a composition should meet the following in vitro dissolution profile:

| Time (hours) | Average % venlafaxine maleate released |
|---|---|
| 2 | <30 |
| 4 | 30–55 |
| 8 | 55–80 |
| 12 | 65–90 |
| 24 | >80 | using USP Apparatus 1 (basket) at 100 rpm in purified water at 37° C. Most advantageously the extended release dosage from meets the above dissolution profile also in 0.1 N HCl aqueous solution.

In terms of in vivo performance, the extended release venlafaxine maleate pharmaceutical composition according to the present invention preferably exhibits on average a maximum venlafaxine blood plasma level not earlier than 4 hours, more preferably not earlier than 6 hours after administration of the composition. Typically the average peak plasma level is reached between 4 and 10 hours, more preferably between 6 and 8 hours after administration. In this regard, a preferred composition is bioequivalent to the commercially available EFFEXOR XR®.

Extended release tablets can be formulated according to any of the known techniques such as those based on matrix technology, osmotic pressure technology, multiparticulates compressed into tablets, multilayer tablets having at least one layer based on one of the foregoing, as well as coated tablets, using known materials and methods.

Tablets employing a matrix, in either a monolithic tablet or in one or more layers optionally built on a tablet core, are generally the most common and frequently the easiest to form from a commercial manufacturing standpoint. The matrix provides a diffusion and/or erosion release of the drug. The matrix is generally composed of at least one type of matrix material selected from hydrophilic (hydrogel), inert, lipophilic, and biodegradable matrix materials. Materials used for each of these kinds of matrices in pharmaceutical oral dosage forms are well known in the art and are briefly described below.

A hydrophilic matrix material is generally a polymeric material that swells upon contact with water to form a diffusion barrier. Suitable materials include cellulose derivatives such as methylcelluloses (i.e. having a viscosity of 400 cP to 4000 cP), hydroxyethylcellulose, HPMC, and sodium carboxymethyl cellulose; polysaccharides such as galactomannanes, potassium alginates, sodium alginates, agar-agar, carrageen, arabic gum, and sterculia gum; polyacrylates such as CARBOPOL 934, EUDRAGIT LD 35; Noveon or polycarbophils; and other water swellable polymers such as polyvinyl alcohol.

Inert matrix materials provide a tortuous path for the drug to escape the dosage form thereby controlling diffusion of the drug. Such materials include ethylcellulose (ETHOCEL).

Lipophilic matrix materials work through a combination of erosion and diffusion. Examples of lipophilic materials include glyceryl palmitosterate (PRECIROL ATO 5), glyceryl behenate (COMPRITOL 888 ATO) and Hydrogenated castor oil (CUTINA HR).

Biodegradable matrix materials also operate through a combination of erosion and diffusion. Biodegradable materials include, for example, polyesters of lactic acid and glycolic acid, polyorthoesters, polyanhydrides and caprolactones. A further description of this technology is set forth in WO02/11701, WO92/04013, and EP 1 005 863.

Because venlafaxine maleate has a surprisingly lower water solubility than venlafaxine hydrochloride, venlafaxine maleate can be more readily formulated into conventional extended release forms including hydrogel tablets. Surprisingly, venlafaxine maleate can even be formulated into a once-a-day extended release hydrogel tablet. A "hydrogel tablet" is one that contains a hydrophilic matrix material that swells or "gels" upon contact with water to thereby slow the diffusion release of the active ingredient. Any of the above-described hydrophilic matrix materials can be used in forming venlafaxine maleate hydrogel tablets of the present invention.

Preferably a hydrogel tablet of the present invention comprises 10%–50% of a venlafaxine maleate compound, preferably a monohydrate form, and 30% to 75% of a hydrogel-forming agent, preferably an HPMC. In some embodiments it may be advantageous for the weight ratio of venlafaxine maleate to hydrogel-forming agent to be in the range of 0.8–1.2:1, preferably approximately 1:1, respectively. In addition to the venlafaxine maleate and hydrogel-forming agent, the composition may further comprise other suitable inert ingredients such as fillers and lubricants in order to assure good properties of the composition in the process of making final medicinal forms, particularly for compression into tablets. Suitable fillers are, e.g. calcium hydrogenphosphate, microcrystalline cellulose or lactose, suitable lubricants are magnesium stearate, precirol, sodium stearyl fumarate (Pruv) or talc.

The tablets of venlafaxine maleate according to the present invention may be produced by any standard tabletting technique, e.g. by wet granulation, dry granulation or direct compression. The tabletting methods that do not employ a solvent ("dry processes") are generally preferable.

In general, dry granulation procedures comprise mixing the solid excipients (except lubricants), compacting the mixture in a compactor (e.g. a roller compactor), or double compression, milling the compacted mass, screening the milled granules, mixing with a lubricant and compressing the mixture into tablets. Direct compression procedures generally comprise mixing the solid excipients in one or more stages and compressing the uniform mixture into tablets. After tablet formation, the tablets may optionally be coated.

The tablets can be of any size and shape. In one preferred embodiment the tablets are small or mini-tablets in size. Small tablets have a diameter of 3–6 mm while mini-tablets have a diameter of 1–3 mm. One or more of the tablets can be taken as such or, more preferably one or more are loaded into a single capsule to provide a unit dose. Most preferably, the small or mini-tablets provide additive amounts of the venlafaxine maleate without modifying the release profile. For example, by making a hydrogel round small tablet of diameter 5 to 6 mm and containing 37.5 mg of venlafaxine (as maleate), capsules containing 37.5 mg, 75 mg, and 150 mg of venlafaxine maleate can be formed by filling a standard No. 0 capsule with 1, 2, or 4 of the small tablets, respectively. Such an additive effect is not as easily obtained with a proportionally larger hydrogel tablet. This is because the release is a function of the volume to surface area ratio.

Scaling up the amount and size of a satisfactory 37.5 mg tablet will likely not result in a satisfactory release profile for the resulting 150 mg tablet, for example, because the volume to surface area ratio is different between the two tablets. For each desired single dosage level, a separate formulation, size and/or shape would be needed. Similar proportionality issues arise with other delayed release tablet technologies. By using small tablets in a single capsule, only one tablet formulation and shape is needed to produce multiple dosage strengths. Typically a small or mini-tablet contains 5 to 50 mg of venlafaxine maleate, especially 10, 25, 30, 37.5, 40, and 50 mg. Depending on the size of the tablet and the capsule from 1 to 10 or more small or mini-tablets can be placed in the capsule.

In addition to filling capsules with small or mini-tablets, an extended release capsule can be formed by filling it with more traditional pellets, beads, and/or spheres. The pellets can be coated with an extended release coating or composition. In addition, different populations of coated pellets can be used in a single capsule, each providing a different release characteristic so that the aggregate release is sustained over a long period; i.e. 12 to 24 hours. Alternatively, the bead population can be substantially homogeneous. A preferred capsule of the pellet type is described in the above-mentioned U.S. Pat. No. 6,274,171 and related EP 0 797 991A1 wherein the venlafaxine hydrochloride used in these patents is replaced with the venlafaxine maleate compound of the present invention.

The venlafaxine maleate compound of the present invention can be used to treat any disease or condition that is treatable by venlafaxine. A venlafaxine-treatable disease or condition is one that could be improved by a serotonin or norepinephrine uptake inhibitor and specifically includes, without limitation, depressions, panic disorder, generalized anxiety disorder, obesity, post-traumatic stress disorder, late luteal phase dysphoric disorder, attention deficit disorders, Gilles de la Tourette syndrome, bulimia nervosa, and Shy Drager syndrome. See published U.S. patent application U.S. Ser. No. 2001/0012855 A1 for a description of the uses of venlafaxine and salts thereof. The venlafaxine maleate compound of the present invention can be used to treat such conditions by administering an effective amount to a patient in need thereof. An effective amount is generally known in the art and/or determined using routine skill. Typically the effective amount for a human is 30 to 300 mg of venlafaxine per day. The patients used herein include human and non-human mammals such as dogs, cats, and horses. The route of administration is not particularly limited and includes peroral, parenteral, and transdermal administration. Preferably, the venlafaxine maleate compound is administered orally via one or two unit dosage forms, especially extended release tablets or capsules, as described above.

The above description and details have been set forth with respect to venlafaxine maleate compounds, but also applies with equal force, mutatis mutandis, to all other low water-soluble venlafaxine salts. The entire disclosure in each of the patents mentioned in the above description is incorporated herein by reference. The invention will be further described with reference to the following non-limiting examples.

EXAMPLES

Example 1

Synthesis of Venlafaxine Hydrogenmaleate

In a 2-liter flask equipped with a mechanical stirrer, 250 g of venlafaxine base was dissolved under heating and stirring in 500 ml of acetone. Then 106.7 g of maleic acid was added to the hot clear solution and the resulting mixture was heated until clear. The clear solution was allowed to cool to room temperature under stirring, and was kept at 4 C. for 30 minutes. The obtained crystals were isolated by filtration, washed with a small amount of acetone and dried overnight under reduced pressure at 40° C.

Yield: 332.3 g.
Identity confirmed by NMR.
No water present (K. Fischer titration)
M.p. 136–138° C., DSC peak at 137.78° C.
HPLC purity: min. 99.9%

Example 2

Round immediate release tablets, 6 mm in diameter, having a venlafaxine dosage strength of 37.5 were made by direct compression having the following ingredients and proportions.

| Ingredients | mg/tablet |
| --- | --- |
| Venlafaxine hydrogenmaleate | 53.125 |
| Microcrystalline cellulose (Avicel PH 102) | 29.875 |
| Lactose monohydrate direct compression | 16.00 |
| Magnesium stearate | 1.00 |

In SGF more than 70% of the venlafaxine was dissolved in 15 minutes.

Example 3

The following extended release hydrogel tablets were made by direct compression:

| Ingredients | Ratio 1:1 | Ratio 1:1.48 |
| --- | --- | --- |
| Venlafaxine hydrogenmaleate | 53.125 | 53.125 |
| HPMC (Methocel K 4M EP) | 53.125 | 78.625 |
| Microcrystalline cellulose (Avicel PH 102) | 12.0 | 12.0 |
| Dibasic calcium phosphate anhydrous (Emcompress) | 5.0 | 5.0 |
| Magnesium stearate | 1.250 | 1.250 |

The invention having been described, it will be readily apparent to those skilled in the art that further changes and modifications in actual implementation of the concepts and embodiments described herein can easily be made or may be learned by practice of the invention, without departing from the spirit and scope of the invention as defined by the following claims.

We claim:

1. A venlafaxine maleate compound.

2. The venlafaxine maleate compound according to claim 1, which is crystalline venlafaxine maleate.

3. The venlafaxine maleate compound according to claim 2, which is crystalline venlafaxine hydrogenmaleate.

4. The venlafaxine maleate compound according to claim 3, which is crystalline venlafaxine maleate anhydrate.

5. The venlafaxine maleate compound according to claim 1, wherein said venlafaxine is pure or substantially pure (+) or (−) venlafaxine enantiomer.

6. A pharmaceutical composition comprising a venlafaxine maleate compound and a pharmaceutically acceptable excipient.

7. The pharmaceutical composition according to claim 6, wherein said excipient is selected from the group consisting of calcium phosphates, microcrystalline cellulose, cellulose derivatives, polyvinylpyrrolidones, sugars, and combinations thereof.

8. The composition according to claim 6, wherein said composition is a unit dosage form and said venlafaxine maleate is contained in an amount between 30 mg and 300 mg, calculated on venlafaxine free base.

9. The pharmaceutical composition according to claim 6, wherein said composition is in the form of a tablet.

10. The pharmaceutical composition according to claim 9, wherein said composition is an extended release composition.

11. The composition according to claim 10, wherein said composition is a hydrogel tablet.

12. The composition according to claim 11, wherein said composition is a once daily dose tablet.

13. The composition according to claim 9, wherein said tablet comprises hydroxypropylmethyl cellulose and venlafaxine maleate.

14. The composition according to claim 12, wherein said tablet comprises hydroxypropylmethyl cellulose and venlafaxine maleate.

15. The composition according to claim 12, wherein said composition has a dissolution profile such that less than 30% of said venlafaxine maleate is released from said composition in 2 hours using either purified water or SGF at 37° C. with stirring at 100 r.p.m. in a basket apparatus.

16. The composition according to claim 15, wherein said composition has a release profile that satisfies the following

| Time (hours) | Average % venlafaxine maleate released |
| --- | --- |
| 2 | <30 |
| 4 | 30–55 |
| 8 | 55–80 |
| 12 | 65–90 |
| 24 | >80 | using USP Apparatus 1 (basket) at 100 rpm in purified water at 37° C.

17. The composition according to claim 6, wherein said composition is in the form of pellets.

18. The composition according to claim 17, wherein said composition is a once daily dose capsule.

19. The composition according to claim 17, wherein said pellets have a dissolution profile that satisfies the following criteria:

| Time (hours) | Average % venlafaxine maleate released |
| --- | --- |
| 2 | <30 |
| 4 | 30–55 |
| 8 | 55–80 |
| 12 | 65–90 |
| 24 | >80 | using USP Apparatus 1 (basket) at 100 rpm in purified water at 37° C.

20. A method for treating a venlafaxine-treatable disease or condition, which comprise administering to a patient in need thereof an effective amount of a venlafaxine maleate compound.

21. The method according to claim 20, wherein said venlafaxine maleate compound is administered in the form of a tablet.

22. The method according to claim 21, wherein said patient suffers from depression and said effective amount of venlafaxine maleate is an antidepressant amount.

23. The method according to claim 20, wherein said venlafaxine maleate compound is administered once daily.

24. The method according to claim 23, wherein said venlafaxine maleate compound is administered orally in the form of one or two tablets once daily.

25. A process for making venlafaxine maleate comprising contacting a venlafaxine substrate and maleate substrate in a suitable solvent, optionally followed by preparation of venlafaxine maleate from the solvent.

* * * * *